United States Patent [19]

Fujioka et al.

[11] Patent Number: 4,668,431
[45] Date of Patent: * May 26, 1987

[54] HYDROXYBORNYLOXYBUTANES AND ORGANOLEPTIC USES THEREOF

[75] Inventors: Futoshi Fujioka, Wanamassa; Richard M. Boden, Ocean; William L. Schreiber, Jackson, all of N.J.

[73] Assignee: International Flavors & Fragrances Inc., New York, N.Y.

[ * ] Notice: The portion of the term of this patent subsequent to Jun. 4, 2002 has been disclaimed.

[21] Appl. No.: 837,348

[22] Filed: Mar. 7, 1986

Related U.S. Application Data

[60] Continuation-in-part of Ser. No. 784,618, Oct. 4, 1985, Pat. No. 4,620,041, which is a division of Ser. No. 644,054, Aug. 24, 1984, Pat. No. 4,619,780, which is a division of Ser. No. 574,150, Jan. 26, 1984, Pat. No. 4,521,634, which is a continuation-in-part of Ser. No. 533,915, Sep. 19, 1983, Pat. No. 4,532,364, which is a continuation-in-part of Ser. No. 507,292, Aug. 1, 1983, abandoned.

[51] Int. Cl.[4] .................... C07L 43/196; C07L 41/06; A61K 7/46; C16B 4/10
[52] U.S. Cl. .................................. 252/522 R; 568/665
[58] Field of Search ...................... 568/665; 252/522 R

[56] References Cited

U.S. PATENT DOCUMENTS 4,619,780 10/1986 Fujioka et al. .................. 568/648 X
4,620,041 10/1986 Fujioka et al. ...................... 568/665

Primary Examiner—Howard T. Mars
Attorney, Agent, or Firm—Arthur L. Liberman

[57] ABSTRACT

Described are mixtures of hydroxybornyloxybutanes defined according to the generic structure:

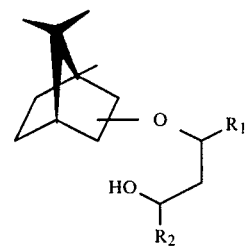

wherein in the mixture in each of the compounds one of $R_1$ or $R_2$ is methyl and the other of $R_1$ or $R_2$ is hydrogen as well as methods for augmenting or enhancing the aroma of consumable materials including perfumes, colognes and perfumed articles by adding thereto an aroma augmenting or enhancing quantity of said mixture of hydroxybornyloxybutanes. The mixture of hydroxybornyloxybutanes of our invention defined according to the structure:

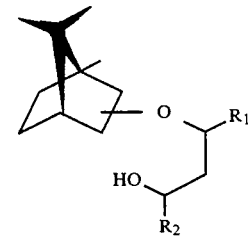

is prepared according to the process of reacting camphene having the structure:

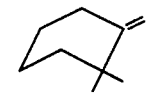

with 1,3-dihydroxybutane having the structure:

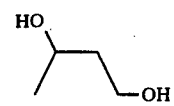

in the presence of an acid catalyst such as a Lewis acid or a protonic acid.

5 Claims, 7 Drawing Figures

FIG. 3 GLC PROFILE FOR FRACTIONS 6-16 OF EXAMPLE I. BULKED DISTILLATION.

GLC PROFILE FOR EXAMPLE II.
CRUDE

FIG. 5 NMR SPECTRUM FOR FRACTION 2 OF EXAMPLE II.

HYDROXYBORNYLOXYBUTANES AND ORGANOLEPTIC USES THEREOF

This application is a continuation-in-part of application for U.S. Patent, Ser. No. 784,618 filed on Oct. 4, 1985 now U.S. Pat. No. 4,620,041, which, in turn, is a divisional of application for U.S. Patent, Ser. No. 644,054 filed on Aug. 24, 1984 now U.S. Pat. No. 4,619,780, which, in turn, is a divisional of application for U.S. Patent, Ser. No. 574,150 filed on Jan. 26, 1984, now U.S. Pat. No. 4,521,634, which, in turn, is a continuation-in-part of application for U.S. Patent, Ser. No. 533,915 filed on Sept. 19, 1983, now U.S. Pat. No. 4,532,364, which, in turn, is a continuation-in-part of application for U.S. Patent, Ser. No. 507,292 deposited on June 23, 1983 and having a filing date of Aug. 1, 1983, now abandoned.

BACKGROUND OF THE INVENTION

The instant invention provides the mixtures of hydroxybornyloxybutanes defined according to the generic structure:

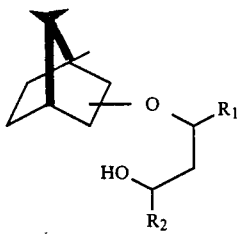

wherein in each of the compounds of the mixture one of $R_1$ or $R_2$ is methyl and the other of $R_1$ or $R_2$ is hydrogen.

Inexpensive woody, cedarwood, incense-like and patchouli-like aromas with incense topnotes are highly desirable in the art of perfumery. Many of the natural materials which provide such fragrances and contribute desired nuances to perfumery compositions as well as perfumed articles including solid or liquid anionic, cationic, nonionic or zwitterionic detergents, perfumed polymers, fabric softener compositions, fabric softener articles, hair preparations, cosmetic powders and the like are high in cost, vary in quality from one batch to another and/or are generally subject to the usual variations of natural products.

U.S. Pat. No. 3,354,225 (Kane) issued on Nov. 21, 1967 (Class 568, Subclass 665) discloses the cedarwood aroma of the compound having the structure:

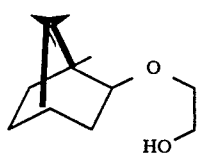

commercially available under the name "Arbinol". The compound having the structure:

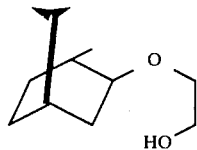

has aroma qualities different in kind and has a substantivity and strength substantially less than the mixture of hydroxybornyloxybutanes of our invention.

BRIEF DESCRIPTIONS OF THE DRAWINGS

FIG. 1 is the GLC profile for the reaction product of Example I of our invention after one hour of reaction, said reaction product containing a mixture of compounds defined according to the generic structure:

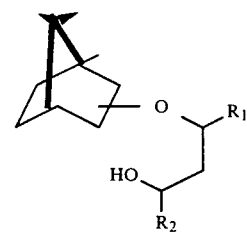

wherein in the mixture in each of the compounds one of $R_1$ or $R_2$ is methyl and the other of $R_1$ or $R_2$ is hydrogen, said mixture including isomers defined according to the structures:

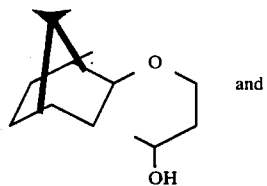

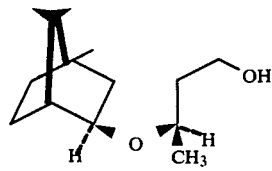

(Conditions: SE-30 column programmed at 160°–220° C. at 8° C. per minute).

FIG. 2 is the GLC profile for the crude reaction product of our invention produced according to Example I defined according to the generic structure:

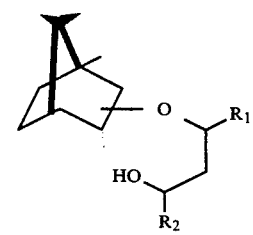

wherein in the mixture in each of the compounds one of $R_1$ or $R_2$ is methyl and the other of $R_1$ or $R_2$ is hydrogen.

FIG. 3 is the GLC profile for bulked distillation fractions 6–16 of the second distillation of the reaction product of our invention containing compounds defined according to the structure:

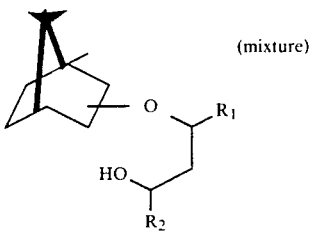

(mixture)

wherein in the mixture in each of the compounds, one of $R_1$ or $R_2$ is methyl and the other of $R_1$ or $R_2$ is hydrogen.

FIG. 4 is the GLC profile for the crude reaction product of Example II containing the mixture of compounds defined according to the structure:

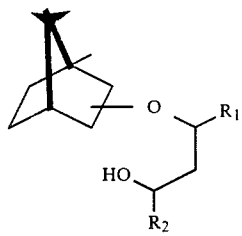

wherein in the mixture one or $R_1$ or $R_2$ is methyl and the other of $R_1$ or $R_2$ is hydrogen.

FIG. 5 is the NMR spectrum for fraction 2 of the distillation product of the reaction product of Example II containing the mixture of compounds defined according to the generic structure:

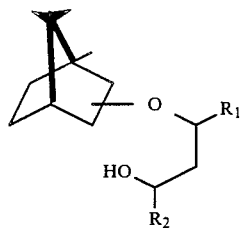

wherein in the mixture in each of the compounds one of $R_1$ or $R_2$ is methyl and the other of $R_1$ or $R_2$ is hydrogen (Conditions: Field strength: 100 MHg; Solvent: $CFCl_3$).

DETAILED DESCRIPTION OF THE DRAWINGS

Figure 6:
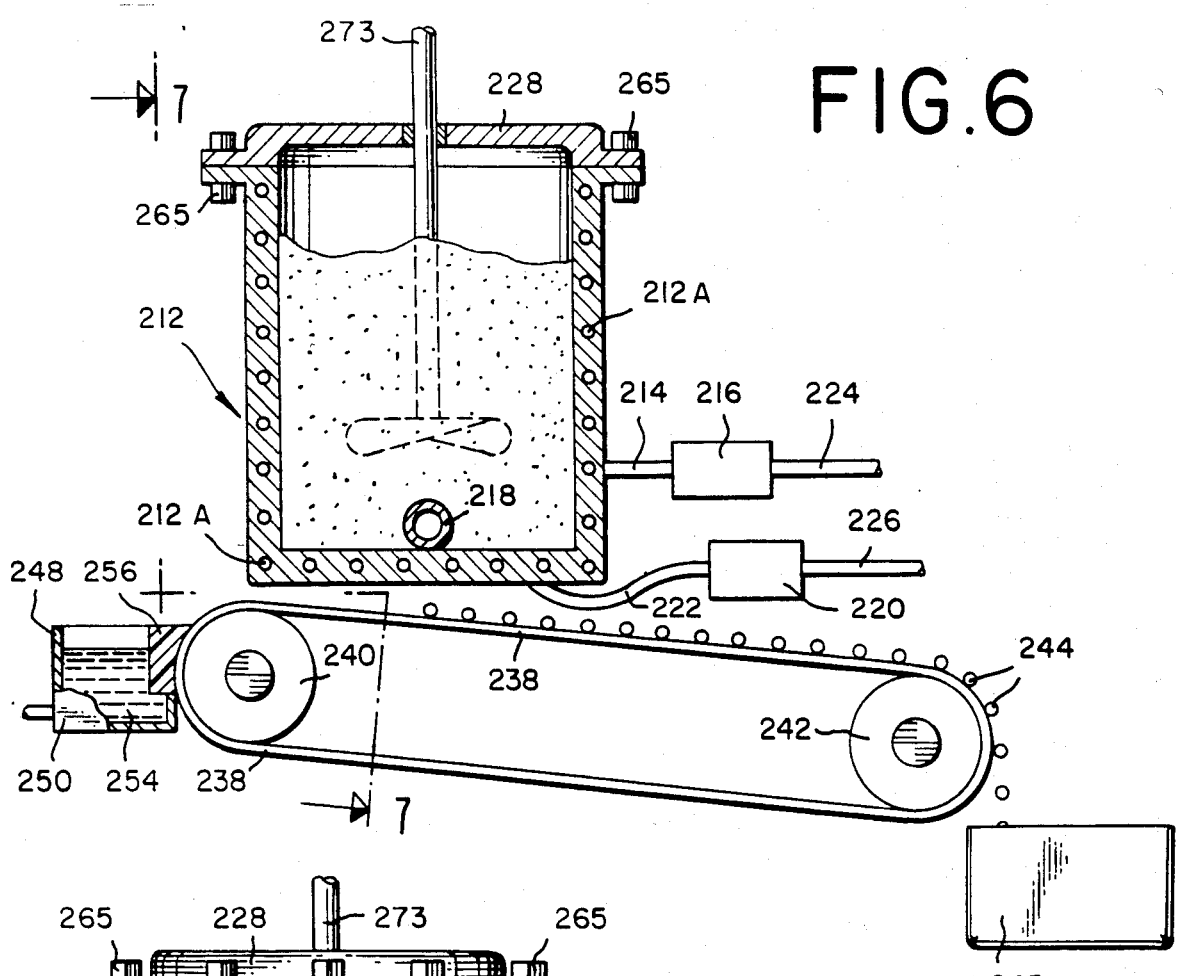
FIG. 6 represents a cut-away side elevation view of apparatus used in forming perfumed polymers which contain embedded therein at least one of the mixtures of hydroxybornyloxybutanes of our invention.
Figure 7:
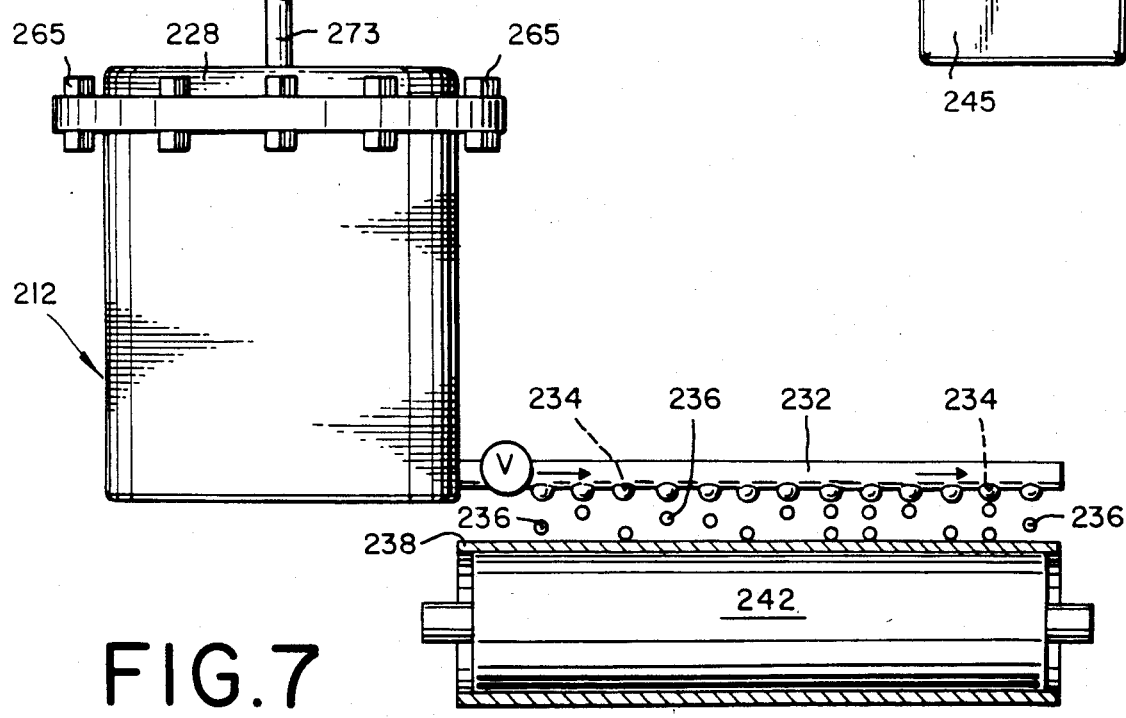
FIG. 7 is a front view of the apparatus of FIG. 6 looking in the direction of the arrows.

Referring to FIGS. 6 and 7, there is provided a process for forming scented polymer elements (wherein the polymer may be a thermoplastic polymer such as low density polyethylene or polypropylene or copolymers of ethylene and vinyl acetate or mixtures of polymers and copolymers such as copolymers of ethylene and vinyl acetate and polyethylene) such as pellets useful in the formation of plastic particles useful in fabricating certain articles which may be perfumed. This process comprises heating the polymer or mixture of polymers to the melting point of said polymer or mixture of polymers, e.g., 250° C. in the case of low density polyethylene. The lowermost portion of the container 212 is maintained at a slightly lower temperature and the material in the container is taken off at such location for delivery through the conduit. Thus, referring to FIGS. 6 and 7, in particular, the apparatus used in producing such elements comprises a device for forming the polymer containing perfume, e.g., polyethylene or polyethylene-polyvinyl acetate or mixtures of same or polypropylene, which comprises a vat or container 212 into which the polymer taken alone or in admixture with other copolymers and the perfuming substance which is a mixture of the hydroxybornyloxybutanes of our invention and other compatible perfumes (if desired) is placed. The container is closed by means of an air-tight lid 228 and clamped to the container by bolts 265. A stirrer 273 traverses the lid or cover 228 in an air-tight manner and is rotatable in a suitable manner. A surrounding cyclinder 212 having heating coils 212A which are supplied with electric current through cables 214 and 222 from rheostats or controls 216 or 220 is operated to maintain the temperature inside the container 212 such that the polymer in the container will be maintained in the molten or liquid state. It has been found advantageous to employ polymers at such a temperature that the viscosity will be in the range of 90–100 sayboldt seconds. The heater 218 is operated to maintain the upper portion of the container 212 within a temperature range of, for example, 220°–270° C. in the case of low density polyethylene. The bottom portion of the container 212 is heated by means of heating coils 212A regulated through the control 220 and the control 216 connected thereto through connecting wires 222 and 214 respectively to maintain the lower portion of the container 212 within a temperature range of 220°–270° C.

Thus, the polymer or mixture of polymers added to the container 212 is heated from 10–12 hours, whereafter the perfume composition or perfume material which contains a mixture of the hydroxybornyloxybutanes of our invention is quickly added to the melt. Generally, about 10–45% by weight of the resulting mixture of the perfumery substance containing a mixture of hydroxybornyloxybutanes of our invention is added to the polymer.

After the perfume material is added to the container 212, the mixture is stirred for a few minutes, for example, 5–15 minutes and maintained within the temperature ranges indicated previously by the heating coil 212A. The controls 216 and 220 are connected through cables 224 and 226 to a suitable supply of electric current for supplying the power for heating purposes.

Thereafter, the valve "V" is opened permitting the mass to flow outwardly through conduit 232 having a multiplicity of orifices 234 adjacent to the lower side thereof. The outer end of the conduit 232 is closed so that the liquid polymer in intimate admixture with a mixture of hydroxybornyloxybutanes of our invention taken alone or taken further together with other perfume substances will continuously drop through the orifices 234 downwardly from the conduit 232. During this time, the temperature of the polymer intimately admixed with the perfumery substance in the container 212 is accurately controlled so that a temperature in the range of from about 240°–250° C., for example, (in the case of low density polyethylene) will exist in the conduit 232. The regulation of the temperature through the controls 216 and 220 is essential in order to insure temperature balance to provide for the continuous dripping or dropping of molten polymer intimately admixed with the perfume substance which is all of or which contains a mixture of hydroxybornyloxybutanes of our invention, through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instantaneously and fall off the end of the conveyor 238 into a container 250 which is advantageously filled with water 254 or some other suitable cooling liquid 254 to insure the rapid cooling of each of the pellets 244. The pellets are then collected from the container 250 and utilized for formation of other functional products, e.g., garbage bags and the like.

THE INVENTION

The present invention provides mixtures of hydroxybornyloxybutanes defined according to the generic structure:

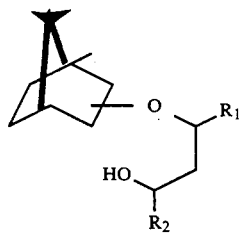

wherein in the mixture, in each of the compounds one of $R_1$ or $R_2$ is methyl and the other of $R_1$ or $R_2$ is hydrogen. Such a mixture of compounds contains a large number of isomers including isomers having the structure:

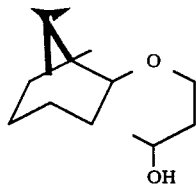

as well optical isomers, for example, those having the structure:

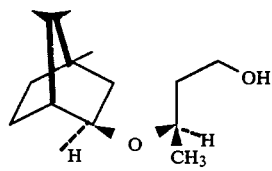

The mixture of hydroxybornyloxybutanes of our invention is prepared according to a process which comprises reacting camphene having the structure:

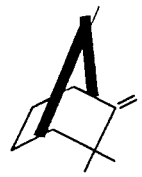

with 1,3-dihydroxybutane having the structure:

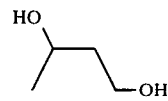

in the presence of an acid catalyst; e.g., a Lewis acid or a protonic acid catalyst. Thus, the reaction for producing the mixture of hydroxybornyloxybutanes of our invention is shown thusly:

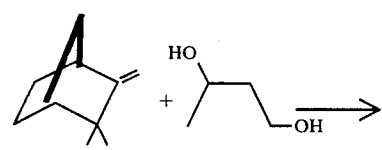

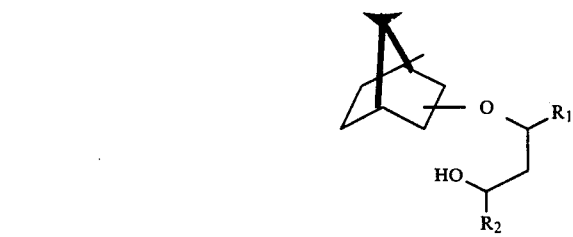

wherein a mixture of compounds is formed and in the mixture in each of the compounds one of $R_1$ or $R_2$ is methyl and the other of $R_1$ or $R_2$ is hydrogen.

The resulting mixture of hydroxybornyloxybutanes of our invention produced according to the process of our invention are capable of augmenting or enhancing the aroma and/or taste of consumable materials including but not limited to foodstuffs, chewing gums, toothpastes, medicinal products, chewing tobaccos, perfumes, perfumed articles, colognes, smoking tobacco and smoking tobacco articles.

Thus, the mixture of hydroxybornyloxybutanes of our invention augment or enhance a cedarwood, incense and patchouli aromas with incense-like topnotes of perfume compositions, colognes and perfumed articles (including but not limited to soaps, anionic, cationic, nonionic or zwitterionic detergents, fabric softener compositions, fabric softener articles, optical brightener compositions, perfumed polymers, hair preparations and the like, thus fulfilling a need in the field of perfumery as well as detergent, cologne, fabric softener and cosmetic manufacture.

In smoking tobacco, smoking tobacco flavoring compositions, substitute smoking tobacco and substitute tobacco flavoring compositions, the mixture of hydroxybornyloxybutanes of our invention produced according to the processes of our invention augment or enhance woody, incense, oriental and patchouli aroma and taste nuances both prior to and on smoking in the mainstream and the side stream.

As stated, supra, the mixture of hydroxybornyloxybutanes of our invention defined according to the generic structure:

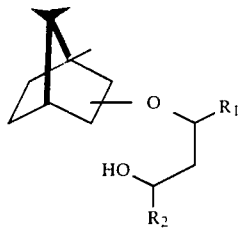

wherein in the mixture one of $R_1$ or $R_2$ is methyl and the other of $R_1$ or $R_2$ is hydrogen may be prepared by reacting camphene having the structure:

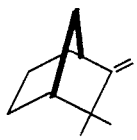

with 1,3-dihydroxybutane having the structure:

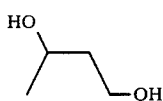

according to the reaction:

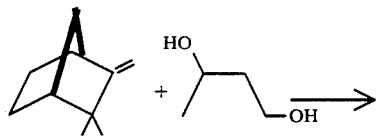

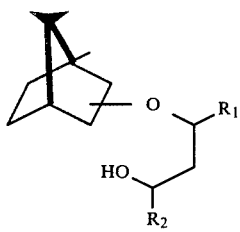

in the presence of a protonic acid catalyst or a Lewis acid catalyst.

Thus, when the reaction takes place in the presence of a catalyst which is a Lewis acid, for example, borontrifluoride etherate, zinc chloride, stannic chloride, diethyl aluminum chloride, ethyl dialuminum chloride or the like, the reaction temperature may range from about 60° C. up to about 100° C. at pressures in the range of from about one atmosphere up to ten atmospheres. Preferably, the reaction when using a Lewis acid takes place at 80° C. at atmospheric pressure and at reflux conditions. The reaction time may vary from about two hours up to about twenty hours depending upon temperature of the reaction. Higher temperatures of reaction give rise to lower times of reaction and lower temperatures of reaction require high times of reaction but a better overall yield of mixture of hydroxybornyloxybutanes of our invention. The mole ratio of 1,3-butanediol having the structure:

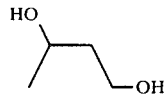

to camphene having the structure:

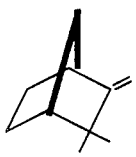

may vary from about 1:2 up to about 3:1 with a mole ratio of diol:camphene of about 2:1 being preferred. At the end of the reaction the reaction mass is neutralized and the reaction product which is a mixture of hydroxybornyloxybutanes defined according to the generic structure:

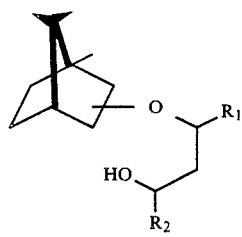

is purified for organoleptic uses as by means of fractional distillation.

When using a protonic acid catalyst, such protonic acids as concentrated sulfuric acid (e.g., 92% aqueous sulfuric acid), concentrated phosphoric acid, paratoluene sulphonic acid and methane sulphonic acid as well as xylene sulphonic acid may be used. When the reaction, to wit:

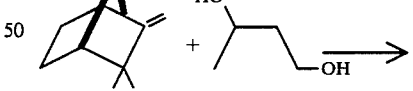

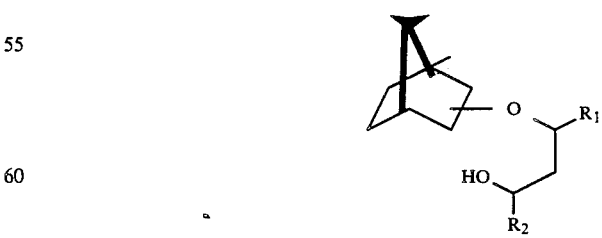

takes place in the presence of a protonic acid, the mole ratio of 1,3-butanediol:camphene may vary from about 3:1 down to about 1:1 with a preferred mole ratio of about 1.5:1 of 1,3-butanediol:camphene. The amount of protonic acid in the reaction mass based on moles camphene reactant may vary from about 0.5% up to about 3% of the camphene reactant with a preferred mole ratio of about 1% of the protonic acid, e.g., concentrated sulfuric acid. The reaction temperature may vary between about 120° C. and about 160° C. with a preferred reaction temperature of from about 135°-150° C. The reaction time may vary from about one hour up to about ten hours. Higher temperatures of reaction give rise to lower times of reaction and lower temperatures of reaction give rise to high times of reaction but a better overall yield. At the end of the reaction the reaction mass is neutralized and the reaction product defined according to the generic structure:

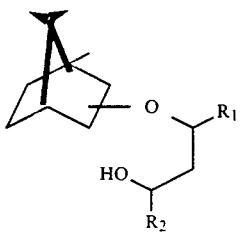

is purified for organoleptic uses by means of fractional distillation.

The mixture o hydroxybornyloxybutanes of our invention and one or more auxiliary perfume ingredients, including, for example, alcohols other than those of our invention; aldehydes; ketones; terpenic hydrocarbons; nitriles, esters; lactones; natural essential oils; and synthetic essential oils may be admixed so that the combined odors of the individual components produce a pleasant and desired fragrance, particularly and preferably in the patchouli, incense and cedarwood fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling, fresh smelling materials.

In perfume compositions, it is the individual components which contribute to their particular olfactory characteristics, however, the overall sensory effect of the perfume compositions will be at least the sum total of the effects of each of the ingredients. Thus, the mixtures of hydroxybornyloxybutanes of our invention can be used to alter, modify, or enhance the aroma characteristics of a perfume composition, for example, by utilizing or moderating the olfactory reaction contributed by another ingredient in the composition.

The amount of the mixture of hydroxybornyloxybutanes of our invention which will be effective in perfume compositions as well as in perfumed articles (e.g., anionic, nonionic, cationic, and zwitterionic solid or liquid detergents, soaps, fabric softener compositions, drier-added fabric softener articles, optical brightener compositions, perfumed polymers and textile sizing agents) and colognes depends on many factors, including the other ingredients, their amounts and the effects which are desired. It has been found that perfume compositions containing as little as 0.05% of the mixtures of hydroxybornyloxybutanes of our invention prepared in accordance with the process of our invention and less than 50% of the mixture of hydroxybornyloxybutanes of our invention or even less (e.g., 0.005%) can be used to impart, augment or enhance patchouli-like, incense-like and cedarwood-like aroma nuances with incense-like topnotes to soaps, cosmetics, solid or liquid anionic, cationic, nonionic and zwitterionic detergents, fabric softener compositions, fabric softener articles, optical brightener compositions, textile sizing compositions, perfumed polymers or other products. The amount employed can range up to 70% of the fragrance components and will depend on considerations, of cost, nature of the end product, the effect desired on the finished product and the particular fragrance sought.

The mixture of hydroxybornyloxybutanes of our invention are useful (taken alone or together with other ingredients) in perfume compositions) as (an) olfactory component(s) in detergents and soaps, space odorants and deodorants, perfumes, colognes, toilet water, bath preparations, such as creams, deodorants, hand lotions and sun screens; powders, such as talcs, dusting powders, face powders and perfumed polymers and articles of manufacture produced from said perfumed polymers, e.g., garbage bags, children's toys and the like. When used as (an) olfactory component(s) as little as 0.2% of the mixture of hydroxybornyloxybutanes of our invention will suffice to impart, augment or enhance intense patchouli-like, incense-like and cedarwood-like aroma nuances with incense-like topnotes to spicy, incense and patchouli formulations. Generally, no more than 6% of the mixtures of hydroxybornyloxybutanes of our invention based on the ultimate end product are required in the perfumed article composition. Accordingly, the range of mixtures of hydroxybornyloxybutanes of our invention in the perfumed article is from about 0.2% by weight of the mixture of hydroxybornyloxybutanes of our invention up to about 6% of the mixture of hydroxybornyloxybutanes of our invention based on the total weight of perfumed articles.

In addition, the perfume composition or fragrance composition of our invention can contain a vehicle or carrier for the mixture of hydroxybornyloxybutanes of our invention. The vehicle can be a liquid, such as, a non-toxic alcohol, e.g., ethyl alcohol, a non-toxic glycol, e.g., propylene glycol or the like. The carrier can also be an absorbant solid, such as a gum (e.g., gum arabic or xanthan gum) or components for encapsulating the composition (such as gelatin as by coacervation) or such as, urea formaldehyde polymer forming a capsule shell around a liquid perfumed center.

Our invention also relates to the utilization of controlled release technology for the controlled release of perfumes into gaseous environments from polymers such as mixtures of epsilon polycaprolactone polymers and polyethylene which polyepsilon caprolactone polymers are defined according to at lease one of the structures:

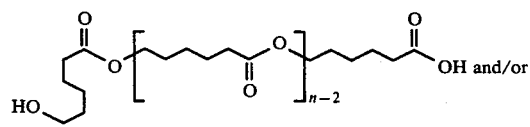

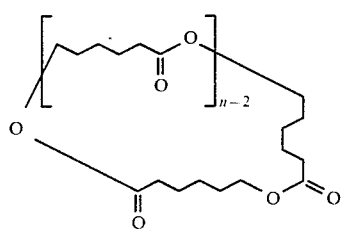

wherein "n" is from about 50 up to about 1,200 with the proviso that the average "n" in the system varies from about 150 up to about 700 according to the mathematical statement:

[700 greater than = n greater than = 150]

with the term "n" being the average number of repeating monomeric units for the epsilon polycaprolactone polymer. The perfumed materials's release rate from such polymer mixture is close to "zero order". As a general rule, the release rate in a polymeric matrix is proportional to $t^{-\frac{1}{2}}$ until about 60% of the functional fluid is released from the polymeric matrix. The release rate thereafter is related exponentially to time as a general rule according to the question:

$$(dM_I/dI) = k_1 e^{-k_2 I}$$

$k_1$ and $K_2$ are constants). According to the Kydonieus, "Controlled Release Technologies: Methods, Theory and Applications" the amount of the perfume composition released is proportional to time as long as the concentration of perfume material present, e.g., the mixture of hydroxybornyloxybutanes of our invention is higher than the solubility of the agent in the matrix. Thus, the dispersed systems are similar to the dissolved systems except that instead of a decreased release rate after 60% of the perfume material has been emitted, the relationship holds almost over the complete release curve. Kydonieus further states, that is one assumes that the release of functional fluid by diffusion if negligible in monolithic erodible systems, the speed of erosion will control the release rate and release by erosion by a surface-area-dependent phenomenon, the release being constant (zero order) as long as the surface area does not change during the erosion process. This is the case with the polymers containing the hydroxybornyloxybutanes of our invention.

The polyepsilon caprolactone polymers useful in practicing our invention are more specifically described in the brochure of the Union Carbide Corporations, 270 Park Avenue, New York, N.Y. 10017, entitled "NEW POLYCAPROLACTONE THERMOPLASTIC POLYMERS PCL-300 and PCL-700". These polyepsilon caprolactone polymers are composed of a repeating sequence of non-polar methylene groups and relatively polar ester groups. The average number of repeating monomeric units varies between 150 and 700 depending on the particular "PCL" number. Thus, regarding PCL-300 the average number of repeating units is about 300. Regarding PCL-700, the average number of repeating monomeric units is 700.

The polyepsilon caprolactone homopolymers which are ultimately taken in admixture with the mixtures of hydroxybornyloxybutanes of our invention may also be stabilized using stabilizers as defined in U.S. Pat. No. 4,360,682 issued on Nov. 23, 1982, the specification for which is incorporated herein by reference. The stabilizing materials which stabilize the polyepsilon caprolactone polymers useful in conjunction with the practice of our invention against discoloration are dihydroxybenzenes such hydroquinone or compounds having the formula:

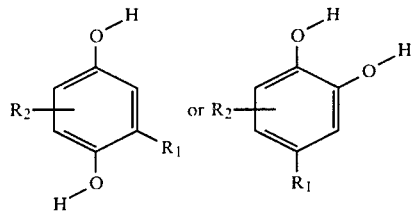

in which $R_1$ is alkyl of from 1 to 8 carbon atoms, and $R_2$ is hydrogen or alkyl of 1 to 8 carbon atoms. It is preferable to have such stabilizers in the polyepsilon caprolactone homopolymer in an amount of from about 100 to 500 ppm. Such stabilizers do not interfere with the mixtures of hydroxybornyloxybutanes dissolved and/or absorbed into the polymeric matrix.

The method of incorporating the mixtures of hydroxybornyloxybutanes of our invention or perfume compositions containing same into the polymers may be according to the techniques of U.S. Pat. No. 3,505,432 issued on Apr. 7, 1970 (the specification for which is incorporated by reference herein) or U.S. Pat. No. 4,247,498 issued on Jan. 27, 1981, the disclosure of which is incorporated by reference herein.

Thus, for example, a first amount of liquid polyethylene/polyepsilon caprolactone polymer mixture (50:50) is mixed with a mixture of hydroxybornyloxybutanes of our invention. Drops are formed from the mixture and the drops are solidified. The solidified drops are then melted, if desired, with a second amount of unscented low density polyethylene, for example, or polypropylene, for example. Usually, but not necessarily, the second amount of polymer is larger than the first amount. The resulting mixture thus obtained, is solidified subsequent to or prior to ultimate casting into a utilitarian shape.

Thus, in accordance with one aspect of our invention, the imparting of scent is effected in two stages. In a first stage, a 50:50 (weight:weight) polyepsilon caprolactone, e.g., PCL-700:polyethylene in molten form is admixed with a high percentage of a mixture of hydroxybornyloxybutanes of our invention and the mixture is solidified in the form or pellets or beads. These pellets or beads thus contain a high percentage off the mixture of hydroxybornyloxybutanes of our invention (e.g., up to 55% by weight of the entire mixture) and may be used as "master pellets" which thereafter, in a second stage, if desired, may be admixed and liquefied with additional polymers such as additional polyethylene or mixtures of polyethylene and polyepsilon caprolactone in an unscented state, or unscented polypropylene. In addition, additional polymers or copolymers may be used, for example, copolymers specified and described in United Kingdom Patent Specification No. 1,589,201 published on May 7, 1981, the specification for which is incorporated by reference herein.

In accordance with the present invention a mixture of hydroxybornyloxybutanes of our invention is added to the polymer in a large closed container or drum which is maintained under controlled temperature conditions while the polymer in a melted condition is mixed with a mixture of hydroxybornyloxybutanes of our invention under agitation.

In order that the perfume be added uniformly to the polymer, the temperature of the melt is constantly controlled during the process. The polymer-perfume mixture is then directed through an elongated conduit or pipe element having a plurality of orifices adjacent to the lower most portion thereof. The polymer enriched with a mixture of hydroxybornyloxybutanes of our invention is permitted to drip through the orifices onto a continuously moving, cooled conveyor upon which the polymer containing a mixture of hydroxybornyloxybutanes of our invention solidifies into small size pellets with the perfume imprisoned therein. The apparatus useful in conjunction with this process, advantageously includes a conveyor of a material which will not adhere to the polymer which contains the mixture of hydroxybornyloxybutanes of our invention.

In order that the droplets form into uniform pellets or beads, the conveyor is continuously washed with a liquid, such as water to maintain the surface relatively cool. The pellets are delivered by the conveyor into a container and packaged for shipment.

Furthermore, the mixture of hydroxybornyloxybutanes of our invention are capable of supplying and/or potentiating certain flavor and aroma notes usually lacking in many smoking tobacco flavors and substitute tobacco flavors heretofore provided.

As used herein in regard to smoking tobacoo flavors, the terms "alter" and "modify", in their various forms, mean "supplying or imparting flavor character or note to otherwise bland smoking tobacco, smoking tobacco substitutes, or smoking tobacco flavor formulations or augmenting the existing flavor characteristic where a natural flavor is deficient in some regard or supplementing the existing flavor impression to modify its quality, character or taste".

As used herein, the term "enhance" is intended to mean the intensification (without change in kind of quality of aroma or taste) of one or more taste and/or aroma nuances present in the organoleptic impression of smoking tobacco or a smoking tobacco substitute or a smoking tobacco flavor.

Our invention thus provides an organoleptically improved smoking tobacco product and additives therefor, as well as methods of making the same which overcome specific problems heretofore encountered in which specific desired inscence-like, patchouli, spicy and oriental aroma and taste nuances prior to and on smoking in both the main stream and in the side stream are created or enhanced and may be readily controlled and maintained at the desired uniform level regardless of variations in the tobacco components of the blend.

This invention further provides various improved smoking tobacco additives and methods, whereby, various woody, incense-like, oriental and patchouli nuances are imparted (on smoking in the main stream and in the side stream) to smoking tobacco products and may be readily varied and controlled to produce the desired uniformed flavor characteristics, particularly, insofar as "oriental" like tobacco characteristics are concerned.

In carrying out this aspect of our invention, we add to smoking tobacco materials or a suitable substitute therefor (e.g., dried lettuce leaves) an aroma and flavor additive containing as an active ingredient a mixture of hydroxybornyloxybutanes of our invention.

In addition to the mixture of hydroxybornyloxybutanes of our invention other flavoring and aroma additives may be added to the smoking tobacco materials or substitute therefor either separately or in admixture with the mixture of hydroxybornyloxybutanes of our invention as follows:
(i) Synthetic Materials
  Beta-ethyl-cinnamaldehyde;
  Beta-cyclohomocitral;
  Eugenol;
  Dipentene;
  Beta-Damascenone;
  Beta-Damascone;
  Maltol;
  Ethyl maltol;
  Delta-undecalactone;
  Benzaldehyde;
  Amyl acetate;
  Ethyl butyrate;
  Ethyl valerate;
  Ethyl acetate;
  2-Hexenol-1;
  2-Methyl-5-isopropyl-1,3-nonadiene-8-one;
  2,6-Dimethyl-2,6-undecadiene-10-one;
  2-Methyl-5-isopropyl acetophenone;
  2-Hydroxy-2,5,5,8a-tetramethyl-1-(2-hydroxyethyl)-decahydronaphthalene;
  Dodecahydro-3a,6,6,9a-tetramethylnaphtho[2,1b]furan;
  4-Hydroxy hexanoic acid, gamma lactone; and
  Polyisoprenoid hydrocarbons defined in Example V of U.S. Pat. No. 3,589,372 issued on June 29, 1971.
(ii) Natural Oils
  Celery seed oil;
  Coffee extract;
  Bergamot oil;
  Cocoa extract;
  Nutmeg oil; and
  Origanum oil.

An aroma and flavoring concentrate containing a mixture of hydroxybornyloxybutanes prepared in accordance with the process of our invention, and, if desired, one or more of the above-identified additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g., lettuce leaves) or mixtures thereof.

The proportions of flavoring additives may be varied in accordance with taste but insofar as enhancement or the imparting or natural and/or spicy notes and/or incense notes and/or patchouli notes we have found that satisfactory results are obtained if the proportion by weight of the sum total of one or more of the mixture of hydroxybornyloxybutanes of our invention is between 250 ppm and 1,500 ppm (0.025%–0.15%) of the active ingredients to the smoking tobacco material. We have further found that satisfactory results are obtained if the proportion by weight of the sum total of the mixture of hydroxybornyloxybutanes of our invention is between 2,500 and 15,000 ppm (0.25%–1.50%).

Any convenient method for incorporation of the mixture of hydroxybornyloxybutanes of our invention in the tobacco product may be employed. Thus, the mixture of hydroxybornyloxybutanes of our invention taken alone or along with other flavoring additives may be dissolved in a suitable solvent, such as ethanol, pentane, diether ether and/or other volatile organic solvents and the resulting solution may either be sprayed on the cured, cased and blended tobacco material or the tobacco material may be dipped into such solution. Under certain circumstances, a solution containing a mixture of hydroxybornyloxybutanes of our invention taken alone or taken further together with other flavoring additives set forth above, may be applied by means of a suitable applicator such as a brush or roller on the paper or leaf wrapped for the smoking product, or it may be applied to the filter by either spraying, or dipping, or coating.

Furthermore, it will be apparent that only a portion of the smoking tobacco or substitute therefore need be treated and the thus treated tobacco may be blended with other tobaccos before the ultimate tobacco product is formed. In such cases, the tobacco treated may have a mixture of hydroxybornyloxybutanes of our invention in excess of the amounts or concentrations above-indicated so that when blended with other tobaccos, the final product will have the percentage within the indicated range.

In accordance with one specific example of our invention, an aged, cured and shredded domestic Burley tobacco is sprayed with a 20% ethyl alcohol solution of a mixture of compounds defined according to the generic structure:

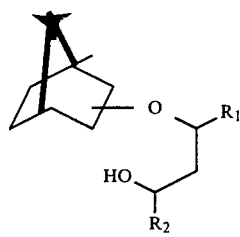

wherein in the mixture in each of the compounds one of $R_1$ or $R_2$ is methyl and the other of $R_1$ or $R_2$ is hydrogen prepared according to Example I, infra in an amount to provide the tobacco composition containing 800 ppm by weight of the above-mentioned mixture of hydroxybornyloxybutanes on a dry basis.

Thereafter, the alcohol is removed by evaporation and the tobacco is manufactured into cigarettes by the usual techniques. The cigarettes, when treated as indicated, have a desired and pleasing aroma prior to smoking which can be described as woody, incense-like, oriental and patchouli-like and on smoking, in the main stream and in the side stream as spicy, oriental-like, turkish tobacco-like, and woody with a slight mouth coating effect.

While our invention is particularly useful in the manufacture of smoking tobacco, such a cigarette tobacco, cigar tobacco and pipe tobacco, other smoking tobacco products formed from sheeted tobacco dust or fines may also be used. Likewise, the mixture of hydroxybornyloxybutanes of our invention can be incorporated with materials such as, filter tip materials, seam paste, packaging materials and the like which are used along with tobacco to form a product adapted for smoking. Furthermore, the mixtures of hydroxybornyloxybutanes of our invention can be added to certain tobacco substitutes of natural or synthetic origin (e.g., dried lettuce leaves) and accordingly, the term "tobacco" is used throughout this specification means any composition intended for human consumption by smoking or otherwise whether composed of tobacco plant parts or substitute materials or both.

The following Examples I and II serve to provide processes for preparing the mixtures of hydroxybornyloxybutanes of our invention. The examples following Example II are illustrative of the organoleptic utilities of the mixture of hydroxybornyloxybutanes of our invention.

All parts and percentages given herein are by weight unless otherwise specified.

EXAMPLE I

Preparation of Sulfuric Acid Catalyzed Reaction Product of Camphene and 1,3-Dihydroxybutane Reaction:

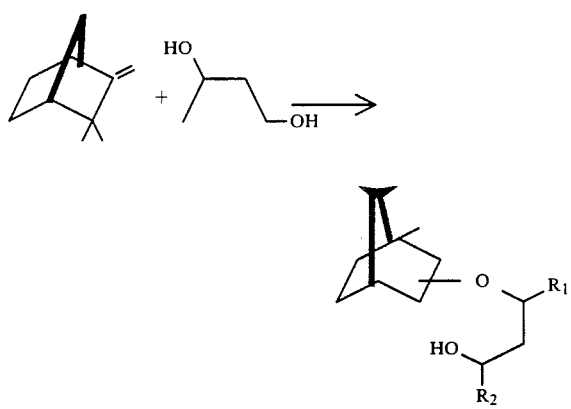

Into a 12 liter distillation flask fitted with stirrer, large condenser, thermometer and dripping funnel, under a nitrogen blanket is placed 2510.0 grams (14.76 moles) of 80% camphene; and 1527.0 grams (16.96 moles) of 1,3-butane diol. With stirring over a period of five minutes, 14.0 grams (0.142 moles of concentrated sulfuric acid (93% sulfuric acid) is added while maintaining the reaction temperature at 45° C.

The reaction mass is then heated to 145° C. with stirring and maintained at a temperature in the range of 137°–145° C. for a period of two hours.

At the end of the two hour reaction period, the reaction mass is cooled to 40° C. and 2 liters of 25% aqueous sodium hydroxide solution is added to the reaction mass. With stirring, the reaction mass is heated to 80° C. and maintained at 80° C. for a period of 15 minutes.

The reaction mass is cooled and separates into two phases; an organic phase and an aqueous phase; the organic phase is distilled on a rushover column yielding the following fractions:

| Fraction No. | Vapor Temp. (°C.) | Liquid Temp. (°C.) | Vacuum mm/Hg. Pressure |
|---|---|---|---|
| 1 | 80/120 | 100/170 | 4.5/3.0 |
| 2 | 128 | 143 | 3.8 |
| 3 | 130 | 143 | 3.8 |
| 4 | 130 | 150 | 3.8 |
| 5 | 130 | 165 | 3.8 |
| 6 | 145 | 170 | 3.5 |

Fractions 2–5 are bulked and redistilled on a 12" Goodloe column yielding the following fractions:

| Fraction No. | Vapor Temp. (°C.) | Liquid Temp. (°C.) | Vacuum mm/Hg. Pressure |
|---|---|---|---|
| 1 | 48/60 | 112/120 | 1.2/1.2 |
| 2 | 80 | 121 | 1/2 |
| 3 | 82 | 122 | 1.2 |
| 4 | 82 | 122 | 1.2 |
| 5 | 82 | 122 | 1.2 |
| 6 | 82 | 122 | 1.2 |
| 7 | 82 | 122 | 1/2 |
| 8 | 83 | 124 | 1.2 |
| 9 | 84 | 123 | 1.0 |
| 10 | 84 | 123 | 1.0 |
| 11 | 85 | 123 | 1.0 |
| 12 | 85 | 123 | 1.0 |
| 13 | 85 | 123 | 1.0 |
| 14 | 85 | 124 | 1.0 |
| 15 | 85 | 125 | 1.0 |
| 16 | 86 | 127 | 1.0 |
| 17 | 87 | 129 | 1.0 |
| 18 | 89 | 133 | 1.0 |
| 19 | 90 | 145 | 1.0 |
| 20 | 101 | 195 | 1.0 |

Figure 1:
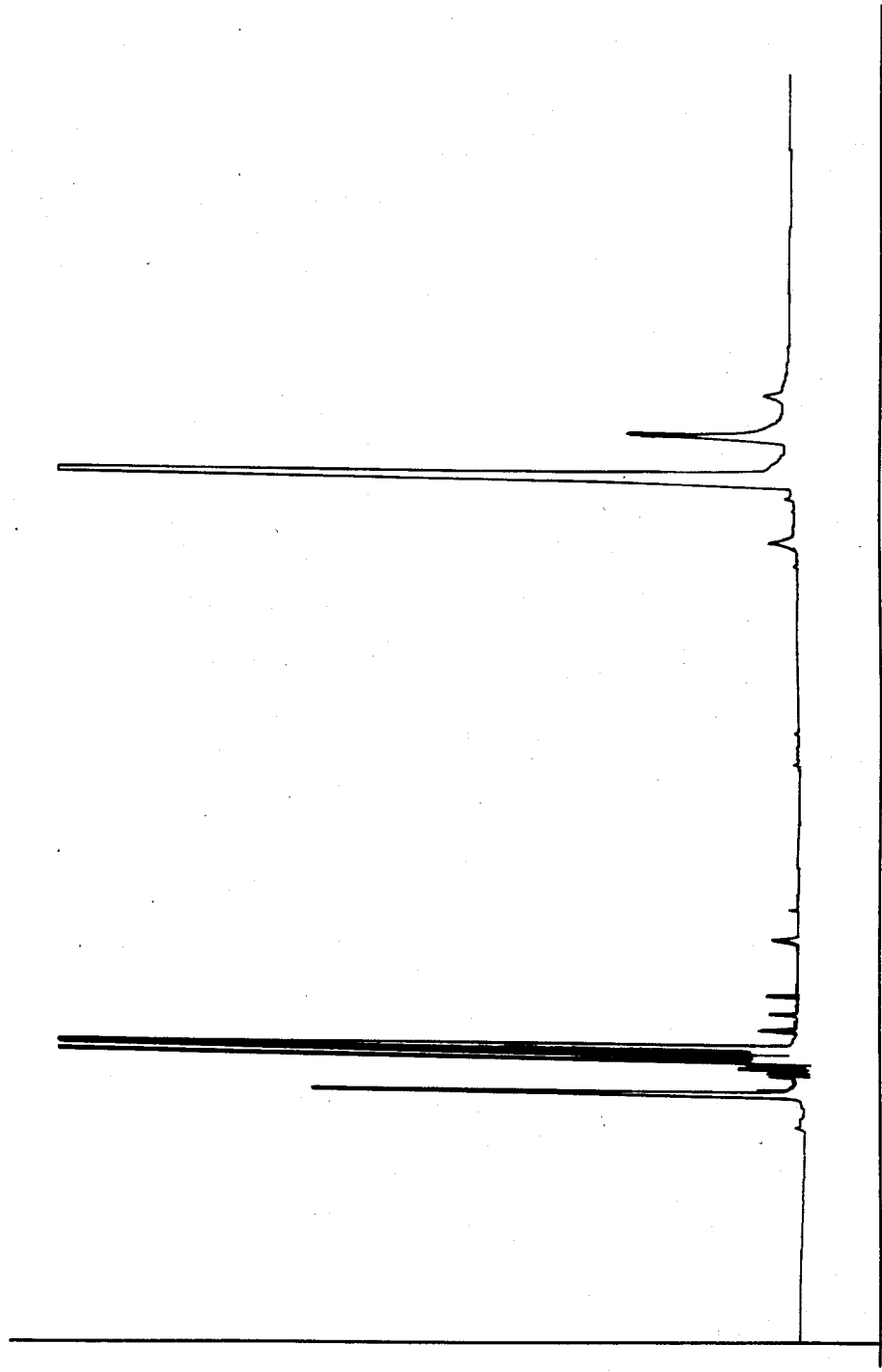

FIG. 1 is the GLC profile for the reaction product after one hour of reaction (Conditions: SE-30 column programmed at 150°–220° C. at 8° C. per minute).

Figure 2:
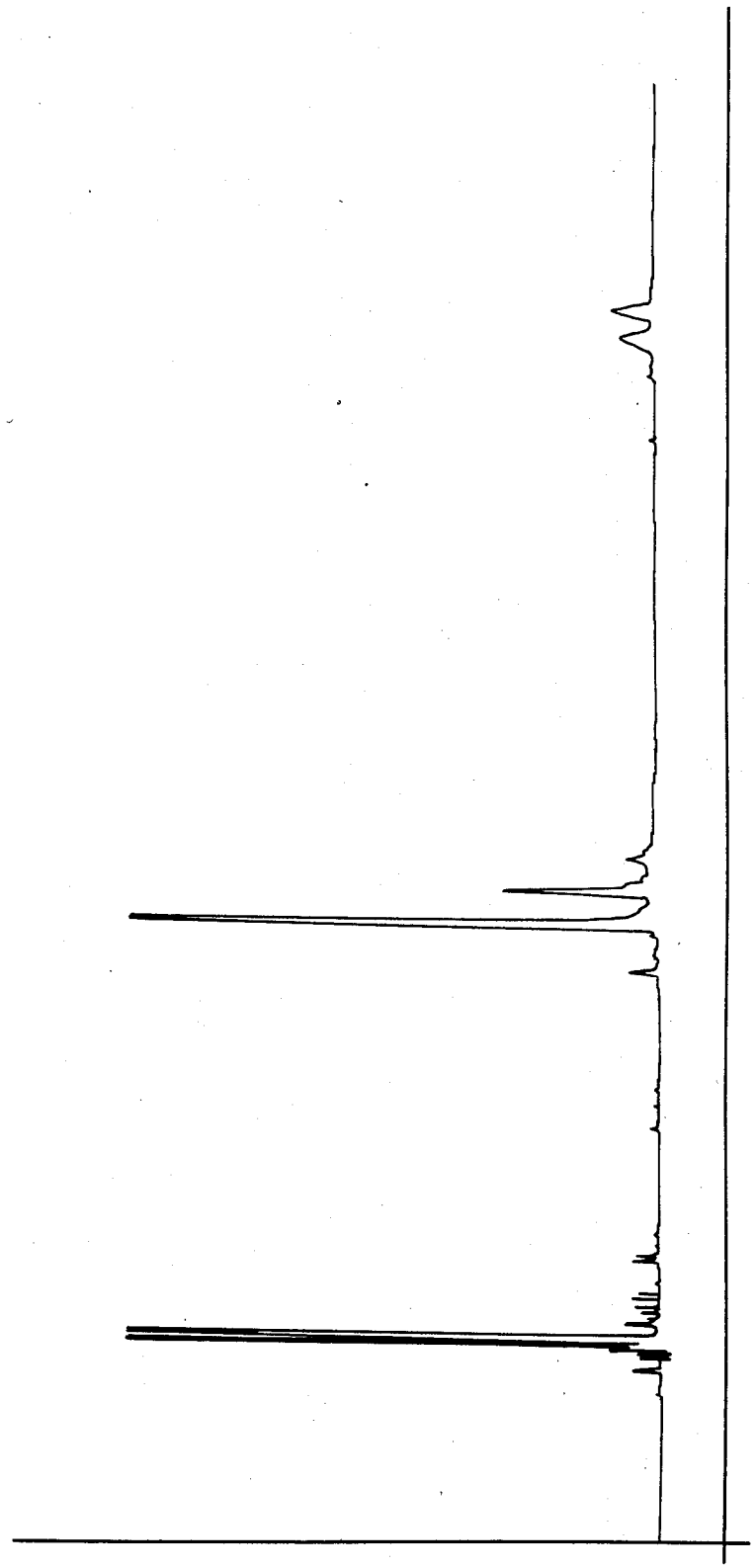

FIG. 2 is the GLC profile for the crude reaction product prior to distillation.

Figure 3:
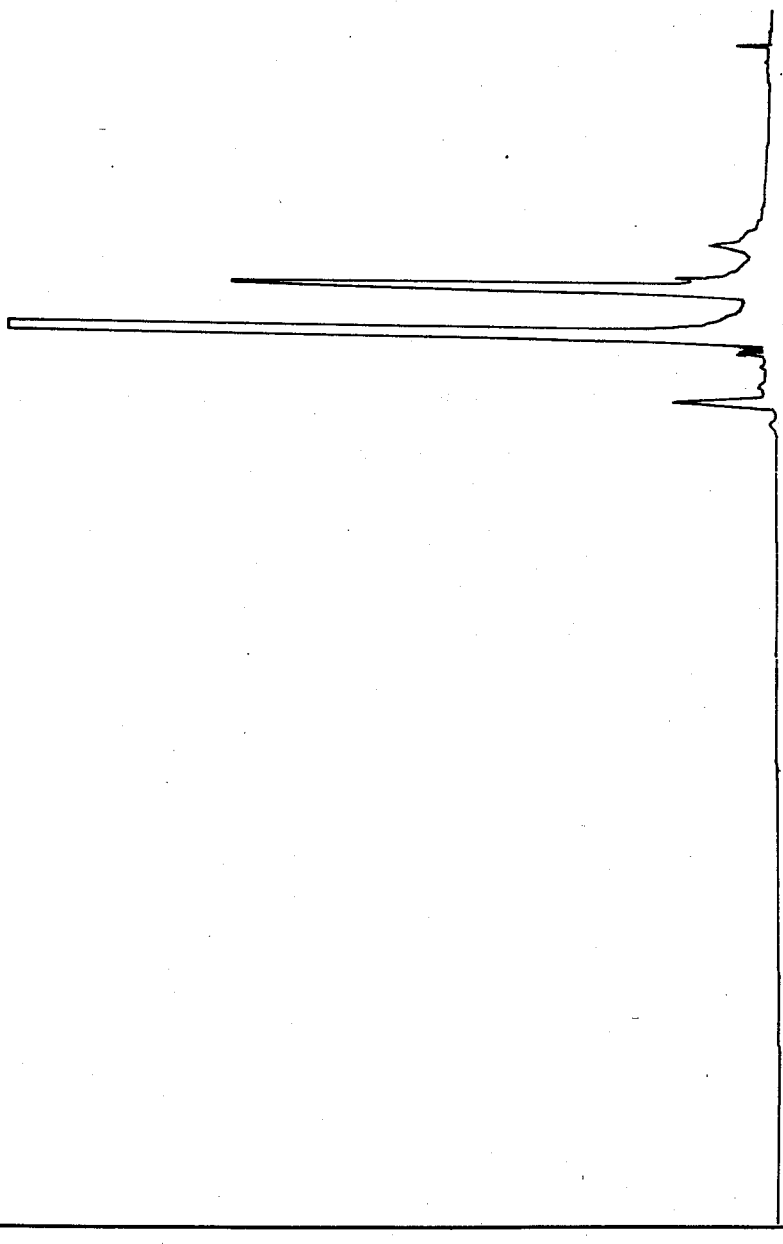

FIG. 3 is the GLC profile for bulked distillation fractions 6–16 of the foregoing second distillation.

EXAMPLE II

Preparation of Mixture of Hydroxybornyloxybutanes

Reaction

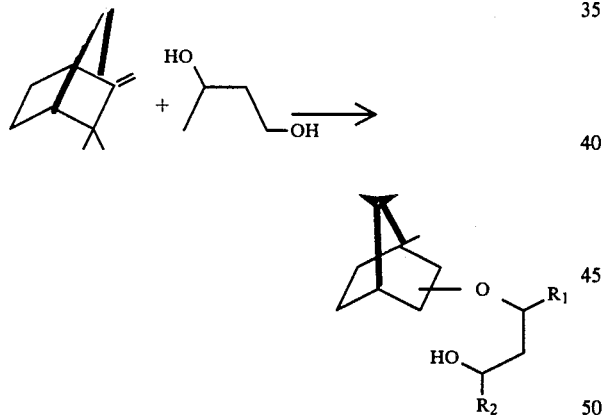

wherein a mixture is formed and in the mixture in each of the compounds one of $R_1$ or $R_2$ is methyl and the other of $R_1$ or $R_2$ is hydrogen.

Into a one liter vessel equipped with a stirrer, thermometer, reflux condenser and heating mentle is placed 340 grams of 1,3-butanediol and 10 grams of boron trifluoride. The reaction mass is heated to 80° C. and while maintaininng the reaction mass at 80° C., 340 grams of camphene is added over a two hour period. At the end of the camphene feeding period, the reaction mass is stirred at a temperature of 80° C. for a period of 18 hours.

After the 18 hour period, the reaction mass is quenched with water and the reaction mass is washed with saturated sodium carbonate solution until neutral. The aqueous phase is separated from the organic phase. The aqueous phase is extracted with toluene and the toluene extracts are added to the organic phase. The resulting organic material is then charged to an evaporator and the toluene solvent is recovered.

The resulting product is distilled on a column packed with splash saddles yielding the following fractions:

| Fraction No. | Vapor Temp. (°C.) | Liquid Temp. (°C.) | Vacuum mm/Hg. Pressure | Weight of Fraction (gms) |
|---|---|---|---|---|
| 1 | 93/ | 127/ | 5.0 | 7.0 |
| 2 | 115 | 127 | 5.0 | 15.0 |
| 3 | 123 | 136 | 4.8 | 211.0 |
| 4 | 175 | 220 | 3.8 | 190.0 |

Figure 4:
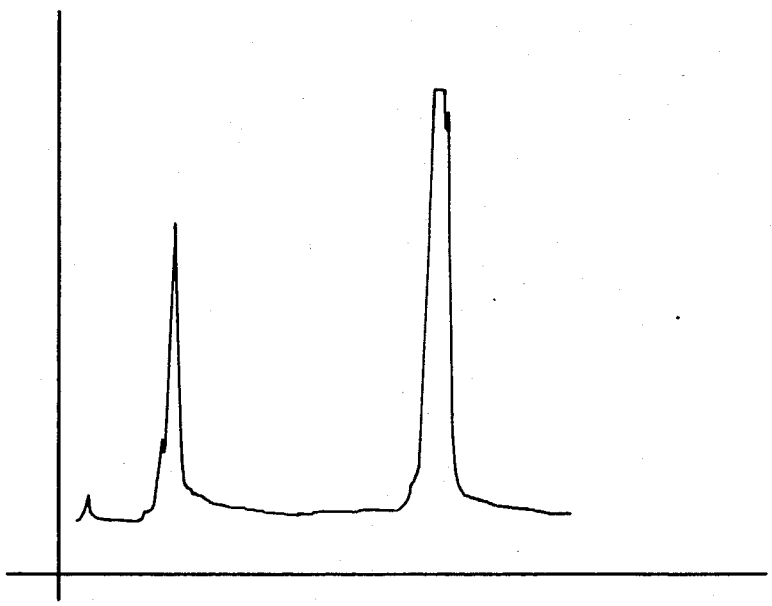

FIG. 4 is the GLC profile for the crude reaction product containing the mixture of compounds defined according to the generic structure:

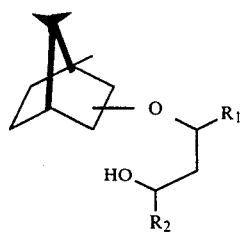

wherein in the mixture in each of the compounds one of $R_1$ or $R_2$ is methyl and the other of $R_1$ or $R_2$ is hydrogen.

Figure 5:
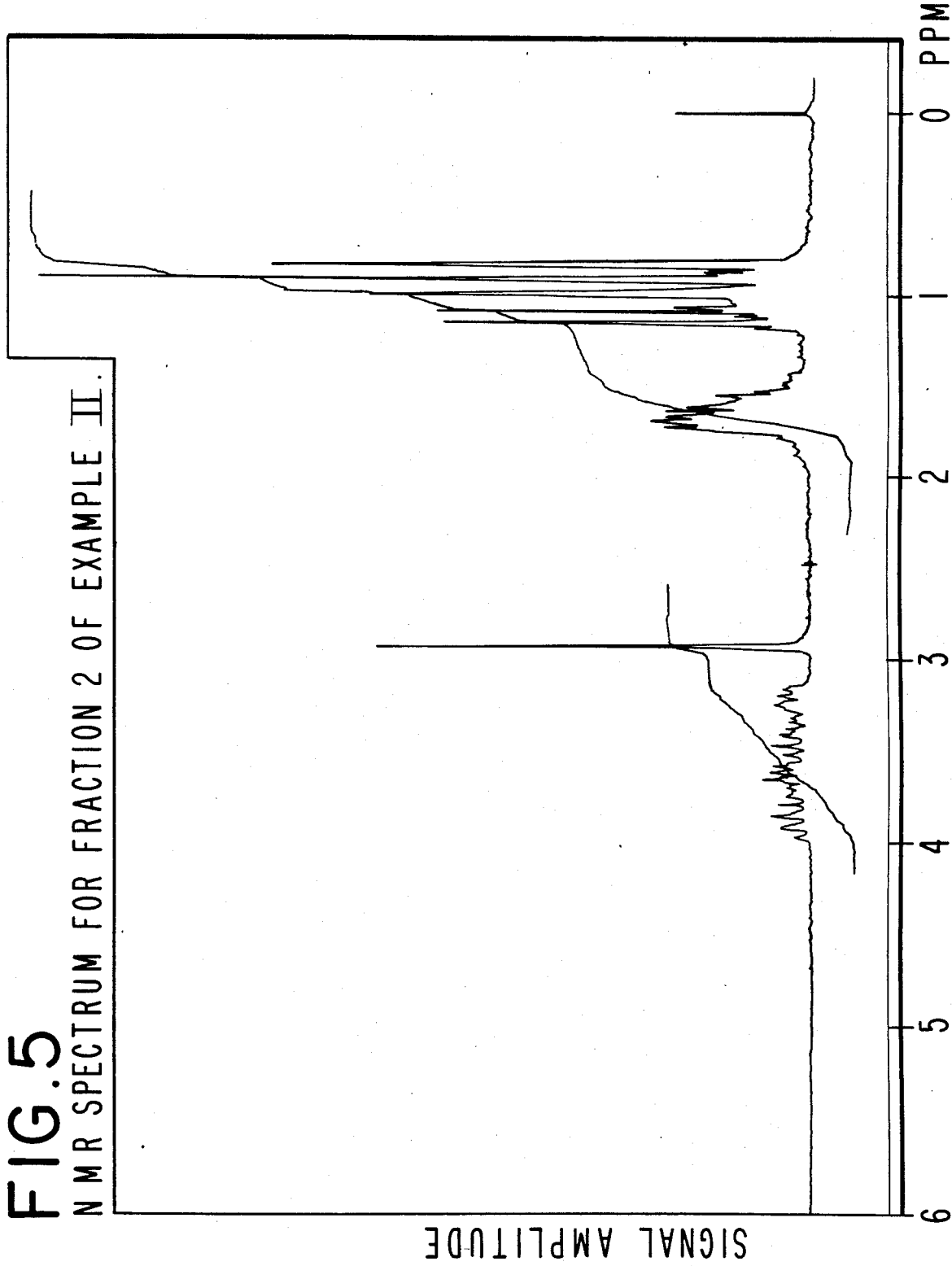

FIG. 5 is the NMR spectrum for fraction 2 of the foregoing distillation product containing the mixture of compounds defined according to the structure:

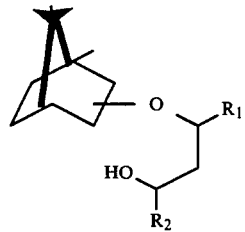

wherein in the mixture in each of the compounds one of $R_1$ or $R_2$ is methyl and the other of $R_1$ or $R_2$ is hydrogen (Conditions: Field strength: 100 MHz; Solvent: $CFCl_3$).

EXAMPLE III

Pine Fragrance

The following pine fragrance formulations are prepared:

| Ingredients | Parts by Weight III(A) | III(B) |
|---|---|---|
| Isobornyl acetate | 100 | 100 |
| Camphor | 10 | 10 |
| Terpineol | 25 | 25 |
| Fir balsam absolute (50% in diethyl phthalate) | 20 | 20 |
| Coumarin | 4 | 4 |
| Linalool | 30 | 30 |
| Fenchyl alcohol | 10 | 10 |
| Anethole | 12 | 12 |
| Lemon terpenes washed | 50 | 50 |
| Borneol | 5 | 5 |
| Galbanum oil | 5 | 5 |

-continued

| Ingredients | Parts by Weight | |
|---|---|---|
| | III(A) | III(B) |
| Turpentine Russian | 150 | 150 |
| Eucalyptol | 50 | 50 |
| 2,2,6-trimethyl-1-cyclohexene-1-carboxaldehyde | 12 | 12 |
| Maltol (1% in diethyl phthalate) | 5 | 5 |
| Mixture of compounds defined according to the structure: | 28 | 0 |

[structure diagram with bicyclic group, O-CHR₁-CH(OH)-R₂ side chain]

wherein in the mixture one of R₁ or R₂ is methyl and the other of R₁ or R₂ is hydrogen prepared according to Example I, bulked distillation fractions 6–16.

| Mixture of compounds defined according to the structure: | 0 | 28 |

[structure diagram with bicyclic group, O-CHR₁-CH(OH)-R₂ side chain]

wherein in the mixture one of R₁ or R₂ is methyl and the other of R₁ or R₂ is hydrogen and each of the compounds produced according to Example II, bulked distillation fractions 2–4.

In each of Examples III(A) and III(B) the mixture of compounds defined according to the generic structure:

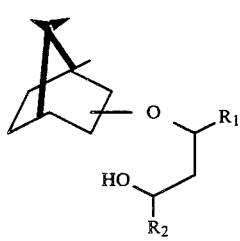

wherein in the mixture one of R₁ or R₂ is methyl and the other of R₁ or R₂ is hydrogen imparts to the pine formulation an intense patchouli, incense and cedarwood aroma and intense incense topnotes. Accordingly, the pine formulation in each of Examples III(A) and III(B) can be described as "piney, with intense patchouli incense and cedarwood undertones and intense incense topnotes".

EXAMPLE IV

Preparation of Cosmetic Powder Compositions

Cosmetic powder compositions are prepared by mixing in a ball mill 100 grams of talcum powder with 0.25 grams of each of the substances set forth in Table I below. Each of the cosmetic powder compositions has an excellent aroma as described in Table I below:

| SUBSTANCE | AROMA DESCRIPTION |
|---|---|
| Mixture of compounds defined according to the structure: [structure diagram] wherein in the mixture in each of the compounds one of R₁ or R₂ is methyl and the other of R₁ or R₂ is hydrogen prepared according to Example I, bulked distillation fractions 6–16. | A cedarwood, patchouli and incense aroma with incense and incense-like topnotes. |
| Mixture of compounds defined according to the generic structure: [structure diagram] wherein in the mixture in each of the compounds one of R₁ or R₂ is methyl and the other of R₁ or R₂ is hydrogen prepared according to Example II, bulked distillation fractions 2–4. | A patchouli, incense and cedarwood aroma profile with incense topnotes. |
| Perfume composition of Example III(A) | A piney, with intense patchouli incense and cedarwood undertones and intense incense topnotes. |
| Perfume composition of Example III(B). | A piney, with intense patchouli incense and cedarwood undertones and intense incense topnotes. |

EXAMPLE V

Perfumed Liquid Detergent

Concentrated liquid detergents with aromas as set forth in Table I of Example IV (which detergents are prepared from Lysine salt of n-dodecyl benzene sulfonic acid as more specifically described in U.S. Pat. No. 3,948,818 issued on Apr. 6, 1976 the specification for which is incorporated by reference herein) are prepared containing each of the substances set forth in Table I of Example IV, supra. They are prepared by adding and homogeneously mixing the appropriate quantity of perfumery substance as set forth in Table I of Example IV in the liquid detergent. The detergents all possess aromas as set forth in Table I of Example IV, the intensity increasing with greater concentrations of perfumery substance of Table I of Example IV, supra.

EXAMPLE VI

Preparations of a Cologne and Handkerchief Perfume

The perfume substances of Table I of Example IV, supra, are incorporated into colognes at concentrations of 1.5%, 20%, 2.5%, 3.0% and 4.0% in 80%, 85% and 90% aqueous ethanols; and into a handkerchief perfume composition at concentrations of 10%, 15%, 20%, 25% and 30% (in 85%, 90% and 95% aqueous ethanols). Distinct and definite aromas as set forth in Table I of Example IV are imparted to the cologne and to the handkerchief perfume compositions.

EXAMPLE VII

Preparation of a Detergent Composition

A total of 100 grams of a detergent powder (a non-ionic detergent powder containing a proteolytic enzyme prepared according to Example I of Canadian Pat. No. 985,190 issued on Mar. 9, 1976 the disclosure of which is incorporated by reference herein) is mixed with 0.15 grams of each of the substances set forth in Table I of Example IV, supra, until substantially homogeneous compositions are obtained. These compositions have excellent aromas as set forth in Table I of Example IV.

EXAMPLE VIII

Preparation of Soap

Each of the perfumery substances of Table I of Example IV are incorporated into soap (LVU-1) at 0.1% by weight of each substance. After two weeks in the oven at 90° F. each of the soaps showed no visual effect from the heat. Each of the soaps manifested an excellent aroma as set forth in Table I of Example IV, supra.

EXAMPLE IX

Preparation of Soap Composition

One hundred grams of soap chips (IVORY ®, registered trademark of the Procter & Gamble Company of Cincinnati, Ohio) are mixed individually with one gram each of the perfumery substances of Table I of Example IV, supra, until homogeneous composition is obtained. The homogeneous composition is then treated under three atmospheres pressure at 180° C. for a period of three hours and the resulting liquid is placed into a soap mold. The resulting soap cakes, on cooling, manifest excellent aromas as set forth in Table I of Example IV, supra.

EXAMPLE X

Preparation of a Solid Detergent Composition

A detergent is prepared from the following ingredients according to Example I of Canadian Pat. No. 1,007,948 the specification for which is incorporated by reference herein):

| Ingredients | Parts by Weight |
| --- | --- |
| "Neodol 45-11" (a $C_{14}$–$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a "phosphate-free" detergent. A total of 100 grams of this detergent is admixed separately with 0.15 grams of each of the perfumed substances of Table I of Example IV, supra. The detergent samples each have excellent aromas as set forth in Table I of Example IV, supra.

EXAMPLE XI

Utilizing the procedure of Example I at column 15 of U.S. Pat. No. 3,632,396 (the specification for which is incorporated by reference herein), a non-woven cloth substrate useful as a drier-added fabric softening article of manufacture is prepared, wherein the substrate, the substrate coating and the outer coating and the perfuming material are as follows:

1. a water "dissolvable" paper ("Dissolvo Paper");
2. Adogen 448 (m.p. about 140° F.) as the substrate coating; and
3. an outer coating having the following formulation (m.p. about 150° F.);

57 percent $C_{20-22}$ HAPS
22 percent isopropyl alcohol
20 percent antistatic agent
1 percent of one of the perfume substances of Table I of Example IV, supra.

A fabric softening composition prepared as set forth above having the above aroma characteristics as set forth in Table I of Example IV, supra, essentially consists of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and outer coating weight ratio of about 1:1 by weight of substrate. The aroma set forth in Table I of Example IV is imparted in a pleasant manner to the headspace in the dryer on operation thereof, using said drier-added fabric softening non-woven fabric.

EXAMPLE XII

Tobacco Flavor Formulation

Cigarettes are produced using the following tobacco formulation:

| Ingredients | Parts by Weight |
| --- | --- |
| Bright | 40.1 |
| Burley | 24.9 |
| Maryland | 1.1 |
| Turkish | 11.6 |
| Stem (flue-cured) | 14.2 |
| Glycerine | 2.8 |
| $H_2O$ | 5.3 |

At the rate of 0.2%, the following tobacco flavor formulation is applied to all of the cigarettes produced with the above tobacco formulation.

| Ingredients | Parts by Weight |
|---|---|
| Ethyl Butyrate | .05 |
| Ethyl Valerate | .05 |
| Maltol | 2.00 |
| Cocoa Extract | 26.00 |
| Coffee Extract | 10.00 |
| Ethyl Alcohol (95%) | 20.00 |
| $H_2O$ | 41.90 |

To 50% of the cigarettes, 50 and 100 ppm of the mixture of compounds defined according to the structure:

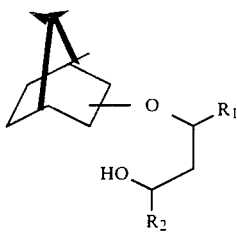

(wherein in the mixture in each of the compounds one of $R_1$ or $R_2$ is methyl and the other of $R_1$ or $R_2$ is hydrogen) produced according to Example I bulked distillation fractions 6–16 are added. These cigarettes are hereinafter called experimental cigarettes and the cigarettes without the mixture of compounds defined according to the structure:

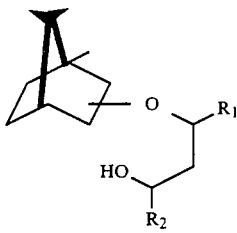

produced according to Example I are hereinafter called "control cigarettes". The control and experimental cigarettes are then evaluated by paired comparison and the results are as follows:

a. In aroma, the experimental cigarettes are found to be more aromatic with a woody, incense, oriental and patchouli aroma and taste.
b. In smoke flavor, the experimental cigarettes are found aromatic, more sweet, more bitter, richer and slightly less harsh in the mouth and more cigarette tobacco-like than the control cigarettes with woody, incense, oriental and patchouli-like aroma and taste nuances.

In summary, the experimental cigarettes containing the mixture of compounds defined according to the generic structure:

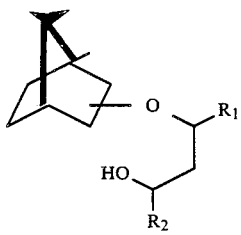

produced according to Example I are found to be woody, incense, oriental and patchouli-like in the main stream and in the side stream.

All cigarettes both control and experimental are evaluated for smoke flavor with 20 mm cellulose acetate filters.

A similar effect occurs when using the mixture of compounds defined according to the generic structure:

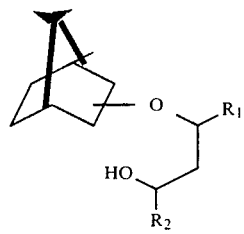

produced according to Example II, bulked fractions 2–4.

What is claimed is:

1. A mixture of compounds defined according to the generic structure:

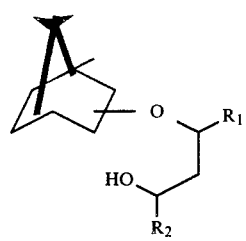

wherein in the mixture in each of the compounds one of $R_1$ or $R_2$ is methyl and the other of $R_1$ or $R_2$ is hydrogen produced according to the process of reacting camphene having the structure:

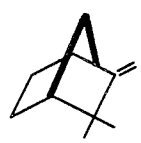

with 1,3-butanediol having the structure:

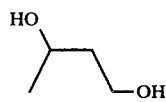

in the presence of an acid catalyst.

2. The product of claim 1 wherein in the process for producing same the acid catalyst is a protonic acid.

3. The product of claim 1 wherein in the process for producing said product, the acid catalyst is sulfuric acid.

4. A process for augmenting or enhancing the aroma of a perfume composition comprising the step of adding to said perfume composition, an aroma augmenting or enhancing quantity of the product of claim 1.

5. A process for augmenting or enhancing the aroma of a perfume composition comprising the step of adding to said perfume composition, an aroma augmenting or enhancing quantity of the product of claim 3.

* * * * *